United States Patent [19]
Schoenwald et al.

[11] Patent Number: 5,961,987
[45] Date of Patent: Oct. 5, 1999

[54] OCULAR PROTEIN STIMULANTS

[75] Inventors: Ronald D. Schoenwald; Charles F. Barfknecht, both of Iowa City, Iowa

[73] Assignee: University of Iowa Research Foundation, Iowa City, Iowa

[21] Appl. No.: 08/742,113

[22] Filed: Oct. 31, 1996

[51] Int. Cl.$^6$ .............. A61K 9/08; A61K 47/32; A61K 47/38; A61K 31/135
[52] U.S. Cl. .............. 424/400; 514/912
[58] Field of Search .................. 424/487, 400, 424/427; 514/912, 915, 654–55, 772.6, 781

[56] References Cited

U.S. PATENT DOCUMENTS

| | | | |
|---|---|---|---|
| 2,997,422 | 8/1961 | Tedeschi | 167/65 |
| 3,050,559 | 8/1962 | Burger | 260/570.5 |
| 3,134,676 | 5/1964 | Ellison | 99/2 |
| 3,153,092 | 10/1964 | Burger | 260/570.5 |
| 3,961,073 | 6/1976 | Snyder | 424/325 |
| 4,016,204 | 4/1977 | Rajadhyaksha | 260/515 R |
| 4,331,687 | 5/1982 | Voelger et al. | 424/330 |
| 4,820,737 | 4/1989 | Schoenwald et al. | 514/654 |
| 5,051,418 | 9/1991 | Schriewer et al. | 514/228.2 |
| 5,340,838 | 8/1994 | Gidda et al. | 514/647 |
| 5,387,614 | 2/1995 | Schoenwald et al. | . |
| 5,424,295 | 6/1995 | Krenitsky et al. | 514/45 |
| 5,459,270 | 10/1995 | Williams et al. | 546/152 |
| 5,658,554 | 8/1997 | Fisher et al. | . |

FOREIGN PATENT DOCUMENTS

| | | |
|---|---|---|
| 873018 | 7/1961 | United Kingdom . |
| 950388 | 2/1964 | United Kingdom . |

OTHER PUBLICATIONS

European J. Opthalmology, 4(3) 1994 pp. 159–165, Martin et al.

*Lacromal Gland, Tear Film, & Dry Eye Syndromes*, Ed. D.A. Sullivan, Pleum Press NY 1994, DARTT pp. 1–9.

Biorganic & Medicinal Chem Lett 6(4) pp. 415–420, 1996, Appelberg et al.

Burger;Yost, Arylcycloalkylamines. I. 2–Phenylcyclopropylamine, *J.Am.Chem.Soc.*, 1948, 70, 2198–2201.

Tedeschi, et al., In vivo Monoamine . . . , *Proc.Soc.Exp., Biol.Med.*, 1960, 103, 680–682.

Heise, et al., Behavioral Determination of Time . . . , *J.Pharmcol.Exp.Ther.*, 1960, 129, 155–162.

Riley, et al., Absolute Configuration of . . . , J.Medicinal Chemistry, 1972, vol. 15, No. 11, 1187–1188.

Arvidsson, et al., N,N–Dialkylated Monophenolic . . . , J.Med.Chem. 1988, 31, 92–99.

*Primary Examiner*—Edward J. Webman
*Attorney, Agent, or Firm*—Zarley, McKee, Thomte, Voorhees & Sease

[57] ABSTRACT

Tear production stimulants of reduced basicity prepared from cyclopropyl adducts of tertiary amines are disclosed.

13 Claims, No Drawings

OCULAR PROTEIN STIMULANTS

FIELD OF THE INVENTION

This invention relates to lacrimal secretion stimulants. It represents an improvement over the invention of our earlier U.S. Pat. No. 4,820,737, issued Apr. 11, 1989.

BACKGROUND OF THE INVENTION

Tear film disturbances account for eye symptoms in millions of Americans. At the present time, treatment primarily consists of replacing a defective tear film with artificial tear substitutes which are sold over-the-counter. The major limitation of these products is their short retention time in the eye. Patients must apply drops as often as every hour to obtain comfort from these products. Recent accomplishments have focused on developing aqueous solutions containing components which will stabilize the tear film or replace specific deficiencies.

A normal tear film is the product of: (1) aqueous secretion by the lacrimal gland and accessory lacrimal glands; (2) secretion of mucous primarily by the goblet cells of the conjunctiva; and (3) lipids secreted by the meibomian gland and the glands of Zeis and Moll in the lids. Mucin, the innermost layer (0.035 $\mu$m), wets the lipophilic epithelial surface of the cornea with the middle aqueous layer. The aqueous layer (7 $\mu$m) contains dissolved proteins, carbohydrates, glycoproteins, oxygen, and inorganic salts. The outer lipid layer (0.1 $\mu$m) retards evaporation of the aqueous component.

Dry eye syndrome, or keratoconjuctivitis sicca (KCS), can occur secondarily to many autoimmune diseases, and as a result of abnormalities in the precorneal tear film physiology. Besides an awareness of a chronically irritable sore eye by the patient, clinicians can diagnose dry eye syndrome by various measurements. These include a tear breakup time of 10 seconds or less in the absence of blinking, or a Schirmer test value of 5 mm or less. The latter involves leaving a standard strip of filter paper under the lower lid for 5 minutes. Other measurements are also helpful and include an observation of a smaller than normal marginal tear strip upon slitlamp examination, and/or a positive rose bengal stain which detects the presence of precipitated mucin and devitalized cells.

The stimulation of aqueous tears by a drug acting on the autonomic nervous system is an approach that had in the past limited success via a systemic route and little success via a topical route of administration. For example, some ophthalmologists have recommended oral ingestion of very dilute solutions of the cholinergic, pilocarpoine, to stimulate tear secretion. However, unpleasant side effects have discouraged widespread use of ingested pilocarpine.

The stimulation of aqueous tears by the systemic or oral route has the undesirable side effect of causing systemic drug reactions by materials such as pilocarpine and other cholinergics. Moreover, by the time the active drug transfers itself through the body to the eye, its effect is significantly diluted. To date, there is no known effective composition for topical route of administration to pharmacologically treat dry eye syndrome.

As earlier indicated, the treatment with tear replacement compositions is not totally satisfactory because of their short retention time in the eye. Often the user of dry eye syndrome tear replacement products must continually apply drops even as often as every hour to obtain eye comfort. Moreover, especially for wearers of contact lenses, this problem of short time retention becomes quite real, rendering tear replacement products unsatisfactory. In short, sufferers of dry eye syndrome are currently, for all practical purposes, excluded from the possibility of wearing contact lenses, since those lenses and their effective use, to say nothing of their comfortable use, necessarily depends upon adequate tear production. Compounds of the earlier patent are indeed quite satisfactory. In fact, they are now in clinical trials. It has, however, been noted in some cases that the tertiary amine molecules of our earlier patent, when applied to the eye, may cause some stinging. Conventional wisdom leads one to the conclusion that the stinging, to the extent that it occurs, is related to the basic (alkaline) nature of the tertiary amines. It has, however, now been surprisingly discovered that tertiary amines, in conjunction with a cyclopropyl adduct, will decrease any stinging sensation, resulting in greater patient comfort and acceptance.

A primary objective of the present invention is to provide tear stimulants that are tertiary amine based which avoid patient eye stinging in those patients that have a tendency toward eye stinging sensation with tear stimulants involving tertiary amines.

Another general objective of the present invention is to provide cyclopropylvinylogous tertiary amine based tear stimulants.

And a still further objective of the present invention is to provide tear stimulants that have decreased side effects when compared to those in our original U.S. Pat. No. 4,820,737.

Another objective of the present invention is to provide a tear stimulant which can be directly applied topically to the eye to minimize side effects and which will stimulate tear production in the eye itself, as opposed to simply acting as a fluid lubricant.

A yet further objective of the present invention is to provide a tear stimulant which has all of the above advantages as enumerated in each of the objectives, and yet provides a sigma agonist component for release of proteins from the lacrimal acini that is at least equal in effectiveness to those mentioned in our earlier U.S. Pat. No. 4,820,737, but causes no eye stinging sensation.

The method and means of accomplishing each of these objectives, as well as others, will become apparent from the detailed description which follows.

SUMMARY OF THE INVENTION

Tear stimulant compositions, which can be topically administered to the eye for treatment of dry eye syndrome, are provided. The compositions contain topically ophthalmically active compounds which are cyclopropyl adducts of tertiary amines, and also their biologically acceptable salt forms. These compounds have reduced basicity, decreased eye stinging tendencies, and enhanced patient comfort, while providing effective natural tear stimulation. Moreover, the compounds are topically effective, and thus systemic side effects are significantly decreased. In another embodiment only single isomers are used, as opposed to racemates, to further enhance effectiveness and minimize side effect risk.

DETAILED DESCRIPTION OF THE INVENTION

In its broadest sense, this invention provides certain compounds that are believed new and most certainly have never been appreciated before for their utility as ophthalmically effective tear stimulants when topically applied to the eye. Compounds useful for this invention have the general formula:

where $R=C_1$ to $C_6$ straight and branched alkyl chains, $R'=C_1$ to $C_6$ straight and branched alkyl chains or $C_3$ to $C_6$ cycloalkanes, and X=H, F, or Cl at the 2, 3, or 4 positions, and W is a pharmaceutically acceptable counteranion, and is preferably hydrochloride, or a sulfate. Other biologically acceptable forms of the compound represented by the general formula may, of course, be employed, and are contemplated for use in this invention as long as they have the necessary organic structure to provide the ophthalmically active tear stimulant when topically administered and are still in a form which is pharmaceutically acceptable for topical administration by generally soluble and acceptable pharmaceutical carriers.

The ophthalmically effective tear stimulant compositions containing the above-described active compounds will generally contain a small but tear stimulating effective amount of the active in an ophthalmically acceptable carrier. On a weight/volume basis it has been found that the amount of active may generally be within the range of about 0.1% to about 5%, and preferably from 0.2% to about 0.6% by weight/volume basis. The amounts of the active compound within these ranges, dissolved in suitable ophthalmically acceptable carriers, have been demonstrated to effectively provide tear stimulation in the tests below-described.

Suitable ophthalmically acceptable carriers are generally known, and, of course, must be non-eye-irritating, non-toxic, and allow for safe, easy eye administration topically. Generally for this invention, aqueous-base systems wherein the carrier includes a buffer system to provide eye safe pH, a viscolyzer to provide suitable viscosity for eye comfort, an antibacterial agent, and a chemical preservative are adequate. The ophthalmically acceptable buffer should provide a composition having a pH within the range of about 5.5 to about 7.8, preferably from about 6.8 to about 7.4. Suitable ophthalmically acceptable buffers can be selected from the water soluble salt forms of citrate, borate, phosphate, carbonate, and acetate.

The viscolyzer suitable for use in this invention should provide the composition with a viscosity within the range of from about 4 centipoises to about 100 centipoises, preferably from about 5 centipoises to about 35 centipoises. Suitable viscolyzers can be selected from the group consisting of hydroxyethylcellulose, hydroxypropyl methylcellulose, methylcellulose and a polyacrylamide sold under the trade name GELAMIDE 250 by American Cyanamide.

In addition, the ophthalmic composition ideally will include antibacterials to provide safety and efficacy for storage stability. The amount of antibacterial can be within the range of from about 0.005% to about 0.2% by weight/volume of the composition. A suitable antibacterial would include, for example, from about 0.005% to about 0.2% by weight/volume of benzalkonium chloride, from about 0.25% to about 0.5% of chlorobutanol, about 0.1% of thimerosal, about 0.05% methylparaben, about 0.01% propylparaben, and sodium chloride in an amount sufficient to make an isotonic solution.

Finally, chemical preservatives may also be used, for example, sodium thiosulfate at about a 0.3% level and ethylenediaminetetracetic acid at about 0.05%. It goes without saying that the precise ophthalmic carrier must be selected to provide pharmaceutical elegance, to provide eye comfort and to allow for effective topical administration. Formulation of such is well within the skill of the ordinary artisan who prepared ophthalmic carrier compositions.

While the ophthalmic compositions of the present invention have been developed primarily to provide a method of topically administering to the eye a composition which treats dry eye syndrome by stimulating the eye's own tear production, it is also contemplated that the compositions of this invention may also be useful in combination with tear substitutes as well.

The following examples are offered to further illustrate, but not limit the invention.

The molecules, as herein described, themselves are in most instances known, although their utility, as expressed herein, is not known. Moreover, methods of synthesis of these compounds are also known. For example, U.S. Pat. No. 2,997,422 (1961) teaches that the methyl analogue of the present type of compounds can be used as an anti-depressant and/or as an anti-hypertensive drug. Since the compounds are known, and it is their utility and composition for ophthalmic use in tear production that is the present invention, a detailed description of their method of preparation need not be given. However, for completeness it is appropriate to have a general discussion of the preparation methodology.

The following examples are offered to illustrate but not limit the invention.

EXAMPLES

The general synthetic procedure for one prototype molecule (±)-N,N-dimethyl-trans-2-phenylcyclopropylamine hydrochloride and its isomers (±)-N,N-dimethyl-trans-2-phenylcyclopropylamine hydrochloride and (−)-N,N-dimethyl-trans-2-phenylcyclopropylamine hydrochloride involves preparation of trans-2-phenylcyclopropylamine as mixture of (+) and (−) isomers by the literature method [Burger, A. B.; Yost, A., *J. Am. Chem. Soc.*, 1948, 70 2198], resolution of the (+)-trans-2-phenylcyclopropylamine and (−)-trans-2-phenylcyclopropylamine by the literature method [Kaiser, C.; Lester, B. M.; Zirkle, C. L.; Burger, A. B.; Davis, C. S.; Delia, T. J.; Zimgibl, L. *J. Med. Chem.* 1962, 5, 1243], and N,N-dimethylation Borch reductive alkylation [Borch, R. F.; Hassid, A. I. *J. Org. Chem* 1972, 37, 1673–4] to (+)-trans-N,N-dimethyl-2-phenylcyclopropylamine and (−)-trans-N,N-dimethyl-2-phenylcyclopropylamine. These literature references disclose conventional preparation techniques, but not the uses of the invention. They are incorporated by reference.

Protein Secretion Rate Assay for (±)-N,N-dimethyl-trans-2-phenylcyclopropylamine hydrochloride in rabbits The rabbits are restrained in boxes and have previously been allowed to acclimatize to the laboratory conditions. Just prior to the dose, baseline tear secretion is measured by placing a Schirmer tear test strip [Clement Clarke Int., Ltd., Harlow, Essex, U.K.] under the lower lid of each eye for five minutes. The right eye of the animal received 50 $\mu$l of the drug formulation, and the other eye receives the vehicle. Proparacaine [25 $\mu$l of 0.5% w/v solution] is instilled 8 minutes before inserting the Schirmer strip. This collection procedure is repeated at 10 and 60 minutes post-dosing. Approximately twenty rabbits are administered drug in the right eye and vehicle in the left eye. Schirmer strips are collected, placed in capped plastic vials, and temporarily stored in dry ice. After 3 hours, the capped vials containing the strips are stored at −20° until they are assayed for protein content.

The protein content of each Schirmer test strip is measured by using a modified Coomassie solution. Bovine serum albumin [BSA, Sigma Chemical Co.] is used as the standard. The tear proteins from a Schirmer strip are extracted with 1 mL of 0.9% sodium chloride in pH 6.24 phosphate buffer [0.066M]. A volume of 0.1 mL of the extract is reacted with 2.5 mL of modified Coomassie reagent in a stoppered quartz cell. After 1 minute the absorbance is measured at 595 nm.

Preparation of modified Coomassie solution. The ingredients, their concentrations, and the order of mixing are as follows: Blue G 250 [BBG, Sigma Chemical Co.] 0.192 g; ethanol [95%] 100 mL; phosphoric acid [85%] 240.0 mL; distilled water qs 2.0 L. After mixing for 12 hours, the solution is filtered 3 to 6 times using standard filter paper [Whatman #1]. The final solution is red, instead of the classic blue Coomassie solution. The modified solution has the advantage of one year stability and, most importantly, is linear over a BSA concentration range of 0 to 200 μg/mL. Once the protein is added to the modified Coomassie solution, the samples are stable for up to five minutes.

Analysis of the results. The protein content of each eye at 10 minutes and 60 minutes post-dosing is calculated as a percent change from baseline. Statistical differences are determined for the dosed eyes compared to baseline.

Protein secretion results:

| | % change from baseline |
|---|---|
| 10 min. drug eye [right] | 43.3 |
| 10 min. control eye [left] | 27.3 |
| 60 min. drug eye | 24.4 |
| 60 min. control eye | 30.6 |

The data here presented shows that in comparison with the control. The compounds here presented are at least as effective as those of our earlier patent. Moreover, the decreased basicity of the compounds indicates clearly that they have less tendency to stinging, and patient discomfort will not be noticed during use. It therefore can be seen that the invention accomplishes at least all of its stated objectives.

What is claimed is:

1. A method of stimulating lacrimal secretion, comprising:

topically applying to the eye to stimulate the eye itself to produce more tears from about 0.1% to about 5% on a weight volume basis of a topical ophthalmic preparation of a compound of the formula:

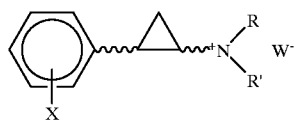

where R=$C_1$ to $C_6$ straight and branched alkyl chains, R'=H, $C_1$ to $C_6$ straight and branched alkyl chains or $C_3$ to $C_6$ cycloalkanes, and X=H, F, or Cl at the 2, 3, or 4 positions, and W is a pharmaceutically acceptable counteranion.

2. The method of claim 1 wherein the amount of said compound is from about 0.2% to about 0.6% on a weight/volume basis of a topical ophthalmic preparation.

3. The method of claim 1 wherein the compound applied to the eye is a biologically acceptable salt form of (±)-N, N-dimethyl trans-2-phenylcyclopropylamine.

4. The method of claim 3 wherein the biologically acceptable salt form is a hydrochloride salt.

5. An ophthalmically effective tear stimulant composition comprising from about 0.1% to about 5% on a weight/volume basis of said composition of a compound of the formula:

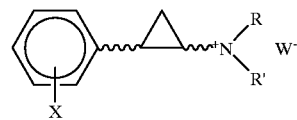

where R=$C_1$ to $C_6$ straight and branched alkyl chains, R'=H, $C_1$ to $C_6$ straight and branched alkyl chains or $C_3$ to $C_6$ cycloalkanes, and X=H, F, or Cl at the 2, 3, or 4 positions, and W is a pharmaceutically acceptable counteranion;

an ophthalmically acceptable viscolyzer for eye comfort and a composition viscosity within the range of about 4 centipoises to about 100 centipoises; and an ophthalmically acceptable buffer to provide a composition having a pH within the range of about 5.5 to about 7.8;

and further providing that the composition is sterile.

6. The composition of claim 5 wherein the pH is within the range of from about 6.8 to about 7.4.

7. The composition of claim 5 wherein the ophthalmically acceptable buffer is selected from the group of water soluble salt forms of citrate, borate, phosphate, carbonate and acetate.

8. The composition of claim 5 wherein the viscolyzer is selected from the group consisting of hydroxyethylcellulose, hydroxypropyl methylcellulose, methylcellulose and polyacrylamide.

9. The composition of claim 5 wherein the carrier includes an antibacterial agent.

10. The composition of claim 5 wherein the carrier includes a chemical preservative.

11. The composition of claim 5 wherein the ophthalmic carrier includes a buffer, a viscolyzer, an antibacterial, and a chemical preservative.

12. A sterile, ophthalmically effective tear stimulant composition comprising from about 0.1% to about 5% on a weight/volume basis of said composition of a biologically acceptable salt form of (±)-N,N-dimethyl trans-2-phenylcyclopropylamine in an ophthalmically acceptable carrier.

13. An ophthalmically effective tear stimulant composition comprising from about 0.1% to about 5% on a weight/volume basis of said composition of a biologically acceptable salt form of a compound of the formula:

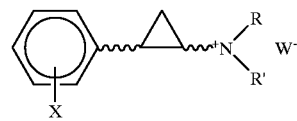

where R=$C_1$ to $C_6$ straight and branched alkyl chains, R'=H, $C_1$ to $C_6$ straight and branched alkyl chains or $C_3$ to $C_6$ cycloalkanes, and X=H, F, or $C_1$ at the 2, 3, or 4 positions, and W is a pharmaceutically acceptable counteranion selected from the group consisting of hydrochloride and sulfate;

an ophthalmically acceptable viscolyzer for eye comfort and a composition viscosity within the range of about 4 centipoises to about 100 centipoises; and an ophthalmically acceptable buffer to provide a composition having a pH within the range of about 5.5 to about 7.8.

* * * * *